US00PP11419P

United States Patent [19]

Kientzler

[11] Patent Number: Plant 11,419

[45] Date of Patent: Jun. 13, 2000

[54] NEW GUINEA IMPATIENS PLANT NAMED 'KISAR'

[75] Inventor: Ludwig Kientzler, Gensingen, Germany

[73] Assignee: Paul Ecke Ranch, Inc., Encinitas, Calif.

[21] Appl. No.: 09/093,285

[22] Filed: Jun. 8, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

| | | | |
|---|---|---|---|
| P.P. 8,457 | 11/1993 | Kientzler | Plt./318 |
| P.P. 9,236 | 8/1995 | Dehan | Plt./318 |
| P.P. 10,107 | 11/1997 | Trees | Plt./318 |
| P.P. 10,300 | 3/1998 | Cosner et al. | Plt./318 |
| P.P. 11,022 | 8/1999 | Bull | Plt./318 |

*Primary Examiner*—Howard J. Locker
*Assistant Examiner*—Kent L. Bell
*Attorney, Agent, or Firm*—C. A. Whealy

[57] ABSTRACT

A new and distinct cultivar of New Guinea Impatiens plant named 'Kisar', characterized by its small and numerous purple-colored flowers; very compact, rounded, mounding, dense and bushy plant habit; short internodes; freely branching habit; and small dark green leaves.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name 'Kisar'.

The new cultivar is a product of a planned breeding program conducted by the Inventor in Gensingen, Germany. The objective of the breeding program was to develop compact varieties with numerous small flowers, early-flowering, uniform plant habit, attractive flower and foliage colors and good flower form.

The new cultivar originated from a cross made by the Inventor of the proprietary selection identified as M 887 as the male, or pollen parent, with the proprietary selection identified as M 494 as the female, or seed parent. The Cultivar 'Kisar' was discovered and selected by the Inventor as a flowering plant within the progeny of the stated cross in a controlled environment in Gensingen, Germany, in April, 1994. Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to br the unique characteristics of 'Kisar'. These characteristics in combination distiguish 'Kisar' as a new and distinct cultivar:

1. Small and numerous purple-colored flowers.
2. Very compact, rounded, mounding, dense and bushy plant habit.
3. Short internodes.
4. Freely branching habit.
5. Small dark green leaves.

Plants of the New Guinea Impatiens are larger and have larger flowers than plants of the male parent, M 887. Compared to plants of the femal parent, M 494, plants of the New Guinea Impatiens are smaller and have smaller flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Kisar'.

The photograph at the bottom of the sheet comprises a close-up view of a typical flower and leaves of 'Kisar'. Flower and foliage colors in the photographs may differ from the actual colors due to light reflectance.

DETAILED BOTANICAL DESCRIPTION

The cultivar 'Kisar' has not been observed under all possible environmental conditions. The phenotype may vary somewhat with variations in environment such as temperature and light intensity, without, however, any variance in genotype. The following observations, measurements and comparisons describe plants grown in 10-cm pots in Encinitas, Calif., under commercial practice in a fiberglass-covered greenhouse with day temperatures ranging from 23 to 29° C. and night temperatures ranging from 16 to 18° C. and light levels of about 3,000 footcandles.

In the following description, color references are made to The Royal Horticultural Society Colour Chart except where general terms of ordinary dictionary significance are used.

Classification:

*Botanical.*—*Impatiens hawkeri* cultivar 'Kisar'.

*Commercial.*—New Guinea Impatiens cultivar 'Kisar'.

Parentage:

*Male parent.*—Proprietary selection of *Impatiens hawkeri* identified as M 887.

*Femal parent.*—Proprietary selection of *Impatiens hawkeri* identified as M 494.

Propagation:

*Type cutting.*—Terminal cuttings.

*Time to intiate roots.*—Summer: About 14 days with 21° C. soil temperature. Winter: About 18 days with 21° C. soil temperature.

*Time to develop roots.*—Summer: About 21 days with 21° C. soil temperature. Winter: About 25 days with 21° C. soil temperature.

Plant description:

*Plant form.*—Very compact, rounded, mounding, upright and somewhat spreading.

*Growth habit.*—Low to moderate vigor. Freely branching, dense and bushy growth. Appropriate for 10 and 12.5-cm containers.

*Crop time.*—From planting of a rooted cutting, about six to eight weeks are required to produce a finished flowering plant in a 12.5-cm container.

*Plant size.*—Height: About 15 cm. Width or spread: About 20 cm.

*Lateral branches.*—Quantity: About seven. Length: About 11 cm. Diameter: About 7 mm. Internode length: About 1.25 cm. Color: 59A/59B.

*Foliage description.*—Leaves simple, generally symmetrical, abundant, opposite or in whorls of four to five, horizontal to plant. Mostly flat. Length: About 7 cm. Width: About 2.2 cm. Shape: Narrowly ovate with acute apex, attenuate base and serrulate margin with ciliation. Texture: Smooth, slightly shiny. Color: Young foliage, upper surface: 147A. Young foliage, lower surface: 147B. Fully expanded foliage, upper surface: Darker than 147A. Fully expanded foliage, lower surface: 147B. Venation, upper surface: 59C to 59D. Venation, lower surface: 59A. Petiole: Length: About 1 cm. Diameter: About 2 mm. Color: 59B.

Flower description:

*Flower type and habit.*—Small purple-colored flowers. Freely and continuously flowering. Flowers arise from leaf axils. Usually about nine flowers per lateral branch. Flowers positioned above foliage and face upward and outward. Flowers flat and rounded. Flowers persistent.

*Flowering season.*—Year-round under greenhouse conditions. In the garden, flowering is continuous from spring until fall. Flowers typically last less than one week depending on environmental and cultural conditions.

*Flower size.*—Length: About 4.1 cm. Width: About 4 cm. Depth: About 7 mm.

*Flower buds.*—Length: About 1.3 cm. Diameter: About 7 mm. Shape: Ovoid. Color: 72A.

*Petals.*—Quantity: Five. Length: Upper petal: About 2 cm. Middle petals: About 2 cm. Lower petals: About 2.5 cm. Width: Upper petal: About 3 cm. Middle petals: About 2.4 cm. Lower petals: About 2.4 cm. Shape: Cordate with slightly emarginate apex, cuneate base and entire margin. Texture: Velvety, slightly iridescence, smooth. Color: When opening, upper surface: Brighter than 74A. When opening, lower surface: 74B/74C. Fully opened, upper surface: Brighter than 74A. Flower color does not fade. Lower two petals have a small lighter pink, 77C, area towards the base and are dark pink, 63A, at the base. Fully opened, lower surface: 74B.

*Spur.*—Length: About 3.5 cm. Shape: Narrow and curved. Color: Proximal, 60B; distal, 59A.

*Peduncles.*—Length: About 2.8 cm. Diameter: About 1 mm. Angle: Upright and outwardly arching. Strength: Moderately strong. Color: 59A/59B.

*Reproductive organs.*—Androecium: Stamen number: Five, anthers fused, filaments free. Anther shape: Obovate. Anther size: 3 mm by 4 mm. Anther color: 158A. Amount of pollen: 158C. Gynoecium: Five-loculate fused. Gynoecium color: 144 A.

Disease resistance: Under commercial conditions, resistance to pathogens has not been observed.

Seed development: Seed production has not been observed.

It is claimed:

1. A new and distinct cultivar of New Guinea Impatiens plant named 'Kisar', as illustrated and described.

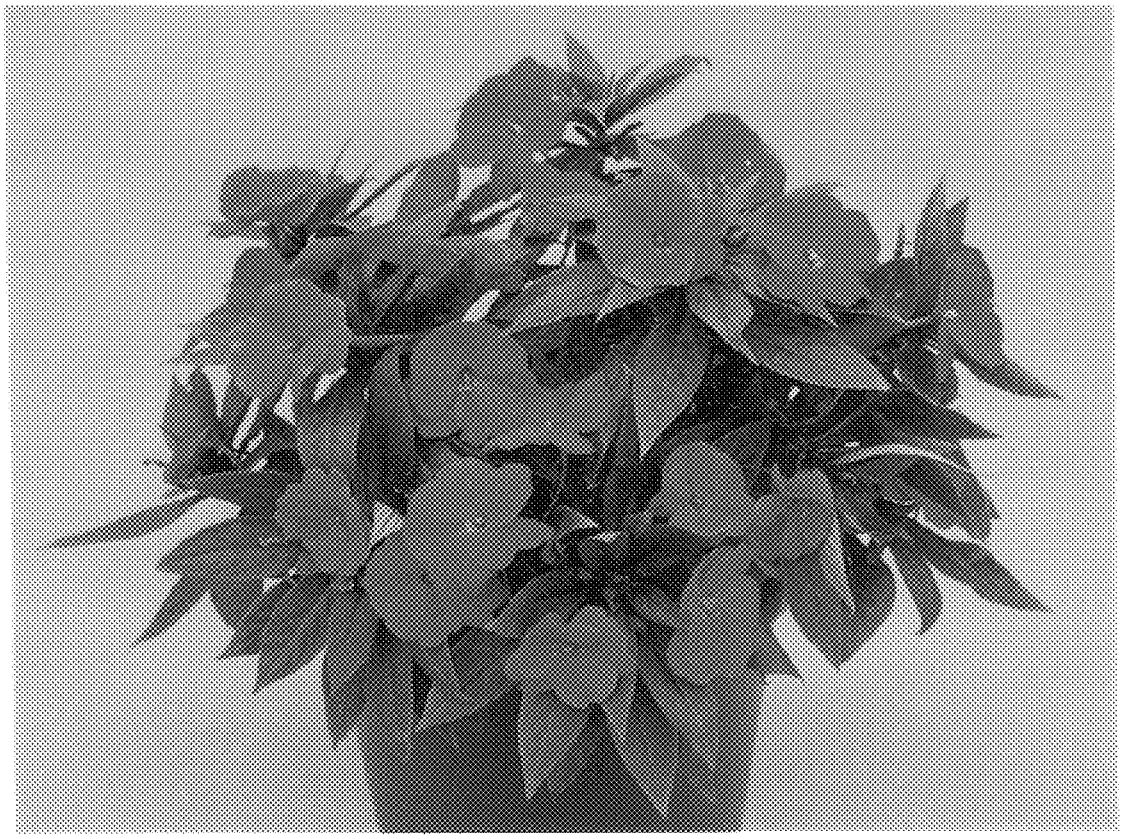
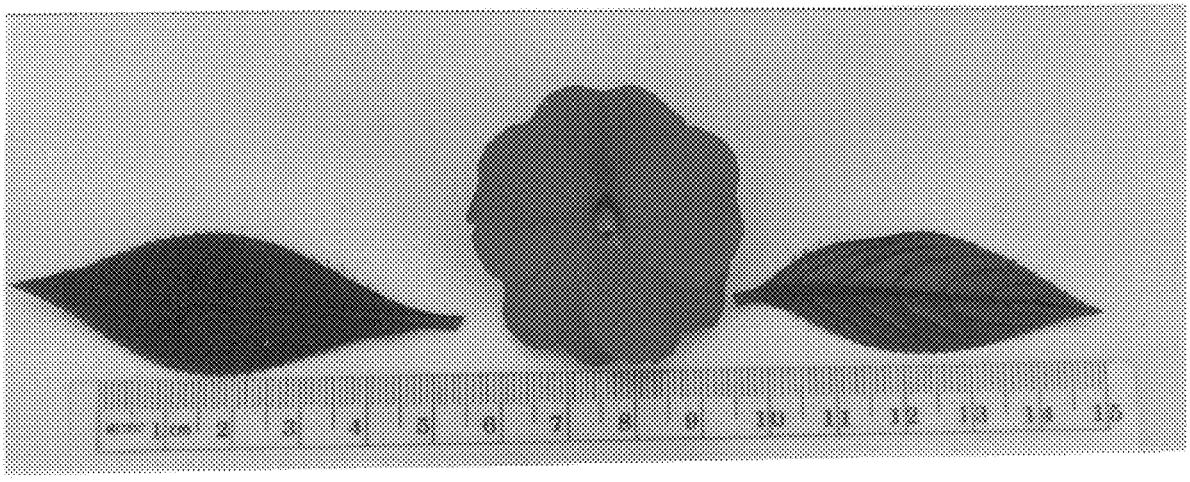

* * * * *